United States Patent
Milosavljevic

(10) Patent No.: US 7,809,510 B2
(45) Date of Patent: Oct. 5, 2010

(54) POSITIONAL HASHING METHOD FOR PERFORMING DNA SEQUENCE SIMILARITY SEARCH

(75) Inventor: Aleksandar Milosavljevic, Woodlands, TX (US)

(73) Assignee: IP Genesis, Inc., The Woodlands, TX (US)

( * ) Notice: Subject to any disclaimer, the term of this patent is extended or adjusted under 35 U.S.C. 154(b) by 791 days.

(21) Appl. No.: 10/375,854

(22) Filed: Feb. 26, 2003

(65) Prior Publication Data
US 2004/0002816 A1    Jan. 1, 2004

Related U.S. Application Data

(60) Provisional application No. 60/359,833, filed on Feb. 27, 2002.

(51) Int. Cl.
*G01N 33/48*  (2006.01)
*G01N 31/00*  (2006.01)
(52) U.S. Cl. .......................................... 702/19; 702/22
(58) Field of Classification Search ................ 702/19
See application file for complete search history.

(56) References Cited

OTHER PUBLICATIONS

Buhler, "Efficient large-scale sequence comparison by locality-sensitive hashing," Bioinformatics, vol. 17 (2001) pp. 419-428.*
Ladunga et al., "FAST-SWAP and FASTA-PAT: Pattern Database Searches Using Combinations of Aligned Amino Acids, and a Novel Scoring Theory," J. Mol. Biol., vol. 259 (1996), pp. 840-854.*

* cited by examiner

*Primary Examiner*—John S Brusca
*Assistant Examiner*—Anna Skibinsky
(74) *Attorney, Agent, or Firm*—Aleksandar Milosavljevic

(57) ABSTRACT

Positional Hashing, a novel method for detecting similarities between texts such as DNA sequences, amino acid sequences, and texts in natural language is disclosed. The method is particularly well suited for large-scale comparisons such as that of mutual comparisons of millions of sequence fragments that result from mammalian-scale sequencing projects and for whole-genome comparisons of multiple mammalian genomes. Positional Hashing is carried out by breaking the sequence comparison problem along its natural structure, solving the subproblems independently, and then collating the solutions into an overall result. The decomposition of the problem into subproblems enables parallelization, whereby a large number of nodes in a computer cluster or a computer farm are concurrently employed on solving the problem without incurring the quadratic time performance penalty characteristic of prior art. Positional Hashing may be used by itself or as a filtering step in conjunction with a variety of sequence comparison algorithms.

12 Claims, 3 Drawing Sheets

Positional hash table for the sampling template (2, 4):

Positional hash keys:          Positional hash bins:

SEQUENCE LISTING

```
<160> NUMBER OF SEQ ID NOS: 3

<210> SEQ ID NO 1
<211> LENGTH: 12
<212> TYPE: DNA
<213> ORGANISM: Artificial Sequence
<220> FEATURE:
<223> OTHER INFORMATION: Artificial sequence created for the purpose of
      describing comparison method.

<400> SEQUENCE: 1
aagtctaaag ct                                                          12

<210> SEQ ID NO 2
<211> LENGTH: 12
<212> TYPE: DNA
<213> ORGANISM: Artificial Sequence
<220> FEATURE:
<223> OTHER INFORMATION: Artificial sequence created for the purpose of
      describing comparison method.

<400> SEQUENCE: 2
```

```
caagaaaaaa ta                                                              12

<210> SEQ ID NO 3
<211> LENGTH: 12
<212> TYPE: DNA
<213> ORGANISM: Artificial Sequence
<220> FEATURE:
<223> OTHER INFORMATION: Artificial sequence created for the purpose of
      describing comparison method.

<400> SEQUENCE: 3
cagagtctgg ac                                                              12
```

POSITIONAL HASHING METHOD FOR PERFORMING DNA SEQUENCE SIMILARITY SEARCH

CROSS-REFERENCE TO RELATED APPLICATIONS

This non-provisional application claims benefit of priority to U.S. Provisional Patent Application Ser. No. 60/359,833 filed Feb. 27, 2002, the entire contents of which are incorporated herein by reference.

FIELD OF THE INVENTION

The invention relates to methods of detecting similarities between nucleic acid sequences, amino acid sequences, and other sequences of symbols over finite alphabets, including texts written in natural language. In a particular embodiment DNA sequences are compared on a cluster of computer nodes where hashing, inversion, and collation steps of the method are performed in parallel, thus significantly increasing the speed of comparison.

BACKGROUND

In this section, we first survey utility of comparative DNA sequence analysis, and then we survey the comparison methods in the prior art, pointing out the problems inherent in the prior art.

Utility of Large-Scale DNA Sequence Comparisons

The utility of large-scale DNA sequencing and comparative analysis is such that the scientific debate is turning away from the question of whether to sequence genomes of additional organisms to the question of which organism should be next selected for sequencing (1, 2, 3, 4, 5). Cross-species comparisons of large genomic regions (8, 9, 10, 11, 12, 13), chromosomes (14), and whole genomes (15) provide a clear demonstration of the power of genome comparison tools in detecting coding exons in genomic DNA sequences of higher organisms and for comparative sequence assembly (16). Recent discoveries (17, 18) further validate early proposals (19, 3) to use the comparative approach for the discovery of up-stream regulatory elements.

Comparative studies at different evolutionary distances reveal biological systems of different degrees of evolutionary age and conservation. For example, intra-mammalian comparisons such as that between human and mouse reveal the evolution and structure of the olfactory system (14) and of imprinting (20), and are generally considered to be one of the main sources of biomedical discoveries in the post-genome era (21). Intra-vertebrate comparisons help us understand the system of chromosomal sex determination (22), while the comparisons across a variety of eukaryotes, such as that between *D. melanogaster*, *C. elegans*, and *S. cerevisiae*, shed light on mechanisms involved in even more basic cellular and developmental processes (15). These comparative studies reveal that a significant number of human genes involved in disease have homologues even in unicellular eukaryotes such as *S. cerevisiae* (15), thus underscoring the power of the comparative method even when it is applied across large evolutionary distances. Comparative sequence analyses have also proven very fruitful in the understanding of microbes. Recent comparative analyses further reinforce the picture of very plastic genomes that readily take up foreign DNA thus acquiring properties such as antibiotic resistance and virulence (23).

Comparative studies do not only include sequence-level comparisons, but also mapping of large-scale genomic rearrangements. Such comparisons use not only finished genomic sequences, but also a variety of other comparative mapping techniques (24, 25, 26). Recent sequencing of the human genome and comparative analyses of whole chromosomal sequences (14, 27) reveal a rich structure of intra- and inter-chromosomal and repetitive rearrangements. Complex repetitive structures appear to play a significant role in genomic rearrangements of significant clinical relevance (28).

Large-scale sequence comparisons are used in the overlap-detection stage of the standard sequence assembly method (29). Moreover, comparison of unassembled reads from one species (e.g., rat) against an assembled genome of another species (e.g., human) can facilitate comparative assembly, thus significantly reducing the total number of sequencing reads and reducing the time to cross-species comparison (16). The computational resources required for comparative assembly (i.e., the multi-CPU-year time required for comparison of multiple mammalian genomes by present methods) have been the main obstacle to implementing this advanced method.

New methods for exchanging annotation and comparative information are based on the Distributed Annotation System (DAS (30)) and are now increasingly used. A major emerging problem is that different assemblies of genomic sequences of the same organism are typically annotated; such assemblies must be compared in order to integrate the annotation information around the assembly of highest quality. Thus, effective methods for large-scale sequence comparison are becoming a bottleneck in the process of utilizing and sharing annotation information.

Problems With Current DNA Sequence Comparison Methods

While the programs such as BLAST (31) and FASTA are well-suited for querying large databases using a limited number of query sequences, they are too slow to handle whole-genome comparisons such as that between complete genomic sequences of human, mouse, rat. They are even less suited to comparing assembled genomes against a rapidly growing database of unassembled reads in publicly available trace archives.

In order to speed the performance of the standard methods, computer clusters and computer farms, often employing thousands of CPUs have been employed. Among most widely used are farms of Intel machines under Linux operating system that utilize the PBS job scheduling system.

The mere addition of hardware does not, however, solve the crucial problem of standard methods: the time requirement that grows quadratically with the number of sequences that are compared in an all-against-all fashion. By multiplying CPUs, the quadratic time is simply divided by a larger number of machines, thus only partially ameliorating the problem at a significant computer hardware cost.

Another approach to solving the problem is pursued by projects such as SSAHA at EBI/Sanger Centre, BLAT at UCSC, and ATLAS at Baylor College of Medicine. These new approaches are all based on constructing an in-memory hash table that serves as a quick lookup index for constant-time similarity search. The main problem with such hashing-based approaches is that the whole hash table must reside in Random Access Memory (RAM) of a single computer. This implies lack of parallelism and requirement for very large RAM.

Two solutions to this problem are typically attempted. The first is to simply employ a single machine with large RAM (>20 GB). The main problem with this solution is that it does not utilize parallelism available on computer clusters, and thus does not scale well to multi-genome comparison problems.

A second solution that is often attempted is to break the sequence database into a number of subsets and to construct hash tables for each subset. The problem with this solution is a time requirement that grows quadratically with the size of the data set (albeit with a smaller constant factor than that encountered by the standard approaches such as BLAST and FASTA).

Thus, despite considerable effort being focused on this problem, there remains a significant need in the art to provide more efficient methods of data manipulation.

SUMMARY OF THE INVENTION

Addressing the limitations of prior art, we here disclose a method for "Positional Hashing," a novel approach to sequence similarity searching. A key to the method is the construction of multiple position-specific hash tables. In the following discussion, we refer to such tables as "positional hash tables".

Each hash table corresponds to a specific sampling template. A sampling template comprises a set of contiguous or non-contiguous diagonally spaced cells. Each compared sequence is sampled horizontally and vertically by projecting a sampling template to obtain a horizontal and vertical hash key for each sequence. If a horizontally sampled sequence and a second vertically sampled sequence hash to the same key, they are then assigned to the same hash bin. This atomic similarity between two sequences is detected in the inversion step.

In the subsequent collation step, atomic similarities along a diagonal or a number of neighboring diagonals are collated together in order to detect overall similarity between pairs of sequences. Hashing, inversion and collation can all be performed independently and concurrently for one or more neighboring diagonals, thus providing means to distribute computation across a multiplicity of CPUs in a multi-processor computer or across a number of nodes in a computer cluster.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 3: Example of Positional Hashing. FIG. 3. illustrates an example where three 12-basepair sequences (X, Y, and Z) insert SEQ ID Nos. 1, 2 and 3, respectively, are compared via Positional Hashing using three sampling templates. The sampling templates consist of three diagonally spaced consecutive cells and are indicated by three distinct shadings (☐, ▨, ▨). Some of the positional hash table bins corresponding to the three sampling templates ((1,2), (4,6), and (7,7)) and the three sequences (X, Y, Z) are illustrated. Similarities in a diagonal and two neighboring diagonals are collated together. Pairwise similarity table for diagonal (1,2) (including entries from its two neighboring diagonals) is illustrated at the bottom.

DETAILED DESCRIPTION OF THE INVENTION

Figure 1:
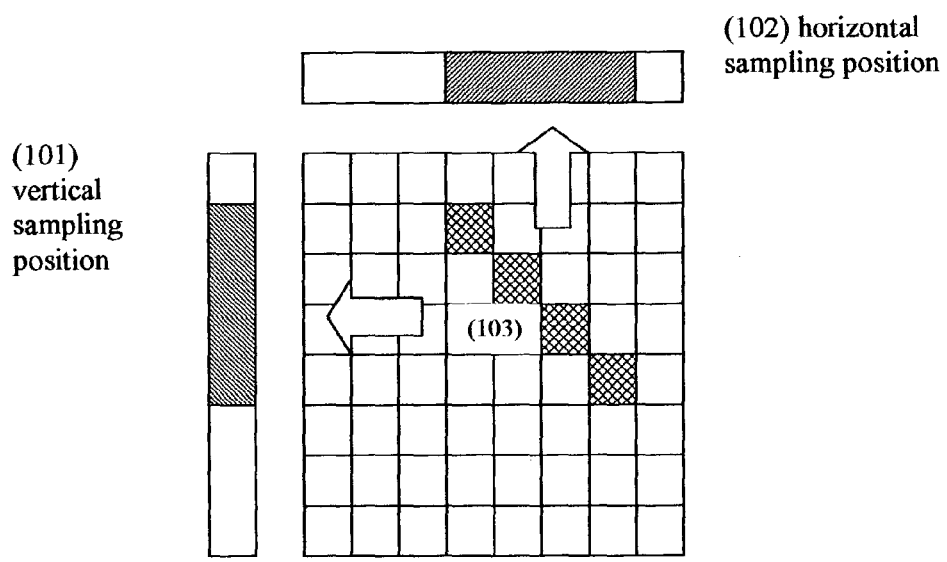
FIG. 1: Positional Hashing method for all-against-all sequence comparisons. Sequences of fixed length are sampled in horizontal (101) and vertical (102) sampling positions, using a particular contiguous four-cell sampling template along a diagonal (103) as a sampling template. A positional hash table is created for each sampling template. Hash bins contain pairs comprising (i) a sequence identifier and (ii) an indicator of sampling position (horizontal or vertical). Positional hash tables may be constructed sequentially within a single-node computer of limited RAM or in parallel on a Linux cluster. Note that sequence p (sampled vertically) and sequence q (sampled horizontally) hash into the same bin of a positional hash table (104), indicating sequence similarity between the two along the respective sampling template. Such similarity matches along templates that occur within the same diagonal or within a set of neighboring diagonals are collated for each pair of matching sequences. The collation also occurs in parallel through localized node-to-node communication involving nearly linear node-to-node communication grid topologies.
Figure 1:
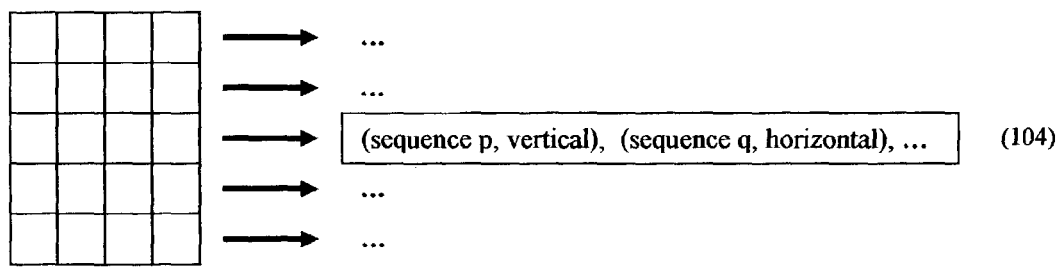

In contrast to previously proposed hashing-based similarity search methods, where each hash table corresponds to a subset of sequence database, each positional hash table of the present invention corresponds to a sampling template in a two-dimensional matrix, as illustrated in FIG. 1. The sampling template is projected both horizontally and vertically onto horizontal and vertical sampling positions. Each sequence is sampled both in a horizontal and in a vertical sampling position, thus producing two, possibly distinct, hash keys per sequence. The hash keys are derived from the letters in the respective horizontal and vertical projections of the sampling template.

Consider a situation where a first sequence is sampled horizontally and a second sequence is sampled vertically using the same sampling template. Consider further the situation where the sequence of letters in the horizontal projection of the sampling template onto first sequence is the same as the sequence of letters in the vertical projection of the template onto second sequence. Thus, the similarity of the two sequences defined by the sampling template would cause them to be placed in the same bin in the positional hash table.

In one particular embodiment, as illustrated in FIG. 1, the hashing step is followed by an inversion step. In the inversion step, bins are inspected for occurrences of pairs of entries where one entry corresponds to one sequence (or sequence fragment) sampled in the horizontal position and the other entry corresponds to a sequence (or sequence fragment) sampled in the vertical position. Each such occurrence is recorded in a new type of hash table that is indexed by pairs of fragment identifiers. Such new type of hash table is referred to as pairwise similarity hash table.

In the pairwise similarity hash table, each bin contains evidence about similarity between a pair of sequence fragments. In one embodiment, the evidence consists of similarities defined by at most a single sampling template. In another embodiment, evidence consists of similarities along multiple sampling templates. In a further specific embodiment, the multiple sampling templates fall within the same diagonal or within a small set of neighboring diagonals. In yet another embodiment, the sampling templates are not restricted to a diagonal or a set of diagonals.

After similarities in sampling templates are detected by inversion of the positional hash table for the specific position, and after the similarities from individual word positions are collated in a bin of a pairwise similarity hash table, a similarity score for pairs of fragments is calculated based on the contents of their respective bins.

Positional Hashing has at least two major advantages over prior art. First, positional hash tables contain only small position-specific subsets of data, and thus do not require large memory, allowing comparison of multiple mammalian-size genome sequences on machines with 1 GB or Random Access Memory (RAM).

Second, because the comparison problem is broken along its natural structure, similarity search can be performed in parallel on any number of available computers without incurring quadratic time penalty characteristic of prior art and without requiring excessive communication complexity (the amount of data that needs to be transferred between nodes of the cluster in the course of computation).

Positional Hashing is not limited to a single algorithm or software—it is rather a widely applicable method for sequence similarity search. It is applicable to searching similarity between DNA sequences, RNA sequences, amino acid sequences, and texts in arbitrary finite alphabets, including texts of scientific abstracts and articles.

Specific embodiment of Positional Hashing may significantly vary from application to application. In one particular application the similarity search performed through Positional Hashing is used in the "filtering" step as part of a two-step DNA sequence similarity search strategy. The filtering is first performed in order to sensitively detect potential similarities (for examples of filtering strategies, see 34) and is followed by a second, "refinement" step, where a more specific, but also more time consuming, similarity search is applied to eliminate false positives that pass the filter. Positional Hashing is useful as part of a variety of filtering procedures and in conjunction with a large variety of "refinement" algorithms such as dynamic programming, Smith-Waterman algorithm, and BLAST algorithm.

While the sampling template illustrated in FIG. 1 is contiguous, present invention is not limited to contiguous sampling templates. In another embodiment, the sampling template may consist of a number of non-contiguous cells in the two-dimensional matrix. In one embodiment, the cells within the sampling template fall within a single diagonal. In another embodiment, the cells fall within at least two diagonals.

The specific embodiment illustrated in FIG. 1 assumes hash keys in the form of DNA subsequences that occur in specific positions in the sampled sequence. In another embodiment, hash key values are calculated from the subsequences by applying an algorithm that transforms the subsequences into the key values. In a further specific embodiment, hash keys are calculated by translating the DNA sequence into amino acid sequence in any of the six orientation/reading frame combinations.

The specific embodiment illustrated in FIG. 1 assumes that DNA sequences are directly sampled. In another embodiment, prior to being sampled in horizontal and vertical sampling positions, the sequences are translated into another sequence of symbols in a possibly different alphabet. In a further specific embodiment, DNA sequence is translated into an amino acid sequence. The translation may occur assuming any combination of the two possible orientations and three possible reading frames.

The specific embodiment illustrated in FIG. 1 assumes that the sequences sampled are DNA sequences. Positional Hashing is equally applicable to detecting similarities between amino acid sequences, natural language texts, and any other texts written in a finite alphabet. In a specific embodiment, the texts of Medline abstracts are compared via Positional Hashing in order to detect abstracts related by subject. In a further specific embodiment, the Medline abstract texts are pre-processed by replacing gene names with their standard synonyms, thus enabling a match between abstracts that refer to the same gene.

While the sequences illustrated in FIG. 1 are of the same length, Positional Hashing also operates on sequences and sequence fragments of different lengths. For the purpose of efficient computer implementation, it is sometimes beneficial to assume that the number of letters (e.g., bases in case of a DNA sequence) in sequences and sequence fragments sampled by Positional Hashing does not exceed some finite number. In one specific embodiment, the number of rows and the number of columns in the comparison matrix are set to that number.

Positional Hashing is not limited to the comparison of short fragments. Long sequences such as full-genome sequences of mammals may be compared. In one particular embodiment, prior to comparing full genomic sequences of two mammals, the genomic sequences are broken into fragments of length 500 bp, with an overlap of 250 bp. The resulting fragments are then compared via positional hashing to identify regions of similarity. Finally, after the comparison is performed, the regions of similarity are mapped back on the original sequence and the pairwise regional similarities are reported using coordinates of the original unbroken genomic sequences.

In one embodiment, similarity between two distinct nucleic sequences is determined by applying Positional Hashing method. In a further embodiment, similarity between three or more distinct nucleic acid sequences is determined by applying the Positional Hashing method. Note that, due to the fact that Positional Hashing method performs an all-against all comparison of fragments, any number of distinct nucleic acids may be compared in an all-against-all fashion.

In a further embodiment, Positional Hashing is performed in order to detect sequence fragment overlaps for the purpose of sequence assembly. In another embodiment, Positional Hashing is performed in order to detect homologous regions between two nucleic acids. In a still further embodiment, Positional Hashing is performed in order to detect orthologous regions between two nucleic acids.

In a still further embodiment, Positional Hashing is performed of sequence fragments from one nucleic acids and assembled sequence of a related nucleic acid in order to perform comparative sequence assembly, as described in claim 1 of U.S. Pat. No. 6,001,562.

Another class of embodiments of Positional Hashing includes, but is not limited to, the clustering of macromolecular sequences. In one such embodiment, EST sequences are clustered to detect groups of ESTs that originate from the same gene or from a group of related genes. In another such embodiment, amino acid sequences are clustered to detect groups of related amino acid sequences. In yet another embodiment, sequences or sequence fragments are first compared via positional hashing and then grouped by mutual similarity and a single element from each group is selected and included in a nonredundant collection. The latter method is especially useful as a tool for selecting nonredundant collections of ESTs and nonredundant collections of text search results, such as the text search results obtained via the Google search engine.

Positional Hashing may be performed in the context of genomic pooling experiments. In one specific embodiment, Positional Hashing is applied to perform Pooled Genomic Indexing. Specifically, Positional Hashing is applied to compare pool reads against a reference nucleic sequence in the deconvolution step of Pooled Genomic Indexing. In another specific embodiment, Positional Hashing is applied to performed Pooled Genomic Indexing. Specifically, Positional Hashing is applied to assemble pool reads in the deconvolution step of Clone-Array Pooled Shotgun Sequencing.

Results obtained through application of Positional Hashing are stored using a variety of tools and formats. In one specific embodiment, the results of Positional Hashing are stored in a tab-delimited format in the GFF format. In another specific embodiment, the results of Positional Hashing are stored in a tab-delimited GTF format. In yet another embodiment, the results obtained through Positional Hashing are stored in a relational database. In a still further embodiment, the results are communicated through the DAS (Distributed Sequence Annotation System) protocol.

Results obtained through application of Positional Hashing are displayed using a variety of tools and formats. In one embodiment, Positional Hashing results are displayed in the form of local sequence alignments, such as those obtained by application of BLAST or Smith-Waterman algorithms. In another embodiment, Positional Hashing results are displayed in the form of long-range sequence alignments, such as those obtained through the application of the BLASTZ and PIP-maker programs. In yet another embodiment, results of Positional Hashing are displayed through a DAS (Distributed Sequence Annotation System) client program. In a still further embodiment, results of Positional Hashing are displayed through a genome browser (such as Ensembl browser at EBI/Sanger Centre in England or that available at the UC Santa Cruz web site).

Creation and inversion of a positional hash table are illustrated in FIG. 1. A positional hash table contains keys defined by a sampling template.

The keys are determined by projecting a sampling template horizontally and vertically. Each sequence is sampled both horizontal and vertical sampling positions, thus providing two entries in the template-specific positional hash table. FIG. 1. illustrates a pairwise comparison matrix with a specific contiguous diagonally spaced sampling template.

Note that the same sequence may result in different keys in horizontal and vertical sampling positions. If the sampling template is on the main diagonal, however, then any sequence hashes to the same key (bin) in both the horizontal and vertical sampling positions.

For simplicity, sequence length and the length of the sampling template (8 and 4 respectively) are chosen to be smaller than in usual applications. In a typical embodiment, sequences of length up to 10,000 basepairs are compared, typically of length 500 bp.

In a typical embodiment, length of sampling templates may vary between four and several hundred basepairs. Sample positions may consist of noncontiguous cells (cells that do not occur next to each other in the similarity matrix). In a specific embodiment, a sampling template may consist of 5-50 randomly selected cells within a diagonal segment of length between 5 and 10,000 basepairs.

One should also note that in one embodiment, both sequences and their reverse complements are sampled and compared. For simplicity, we do not include reverse complements in our illustrative examples.

In the example in FIG. 1, sampling template consists of 4 cells and thus each bin of the templates's positional hash corresponds to a specific 4-letter subsequence in the 4-letter alphabet of DNA. Each hash bin contains zero or more entries. An entry indicates that a sequence contains the bin-specific subsequence along a (horizontal or vertical) projection of a sampling template. Each entry comprises an identifier of a sequence and a binary indicator of sampling position (vertical or horizontal). In the example in FIG. 1, sequence p sampled vertically and sequence q sampled horizontally both hash into the same bin, indicating that both sequences contain the same (bin-specific) subsequence along the sampling template.

Positional hash tables may be constructed sequentially within a single-node computer of limited RAM or in parallel on a Linux cluster. A positional hash table comprises keys obtained by one sampling template. In some instances where enough RAM is available, a single positional hash table may contain sampling information obtained by applying multiple sampling templates. In such cases, the hash key is augmented by the identifier of the sampling template.

Upon construction of positional hash tables, the bins are examined for occurrence of pairs of entries in the same bin such that the entries correspond to two different sequences sampled in two different sampling positions (one sampled horizontally, the other vertically). Each such pair indicates similarity of the two sequences along the respective sampling template. Such similarity is called "atomic similarity". The detection of atomic similarities is referred to as the "inversion step".

Atomic similarities detected in the inversion step are collated into the bins of a pairwise similarity hash table. The keys of a pairwise similarity hash table comprise pairs of sequence identifiers. All atomic similarities detected between two sequences are collated into one bin. The process of building the pairwise similarity table is referred to as the "collation step".

Note that a pairwise similarity hash table contains information from one or more positional hash tables. Thus, while positional hash tables may be created and inverted within a RAM of a single node in a cluster configuration, the collation step may involve significant node-to-node communication. The node-to-node communication topologies are typically close to linear due to the fact that sampling positions that are within a diagonal or within a closely spaced set of diagonals are typically collated together.

In another case, because the positional hash tables and inverted tables have been used (by exploiting inherent parallelism) to produce the much smaller pairwise similarity hash tables, collation is possible on a single, 1-CPU, medium-RAM machine in good time. This is the preferred implementation in the situation where pairwise similarity tables are small. If, on the other hand, pairwise similarity tables are large and require significant time to compute, and if sufficient node-to-node bandwidth is available (such as in a cluster configuration), then pairwise similarity computation itself may be distributed across a number of nodes in a computer cluster.

One or more pairwise similarity tables may be constructed. In one embodiment, a pairwise similarity table is constructed for each diagonal in a comparison matrix and the atomic similarity information from sampling positions within a diagonal is collated into the same pairwise similarity table. In another embodiment, only one pairwise similarity table is constructed and the atomic similarity information from all sampling templates is collated into the same table. In yet another embodiment, a pairwise similarity table is assigned to each diagonal and such table collates atomic similarities obtained from sampling templates within the diagonal and two neighboring diagonals.

The information in individual bins of a pairwise similarity table is used to score the similarity of two sequences. We refer to this process as "similarity scoring". Similarity score is calculated based on the contents of a bin in the pairwise similarity table (comprising atomic similarities collated into the bin) plus, possibly any additional information that may be available.

The similarity scores produced in the scoring step are either used directly or may be used to select pairwise similarities for a subsequent refinement step. The refinement step is aimed at filtering out false similarities that may receive high similarity scores. The refinement step typically employs a more specific but more time-consuming algorithm such as dynamic programming, Smith-Waterman, or BLAST.

If the refinement step is included, then Positional Hashing in effect acts as a filtering step for the more specific refinement algorithm. The filtering step typically must achieve a low false-negative rate (must sensitively detect similarities) while a relatively high false-positive rate (low selectivity) may be acceptable due to the fact that the false positives are eliminated in the refinement step. Of course, a large false positive rate of the filtering step implies more computational effort in the refinement step due to the fact that all putative similarities need to be examined.

Figure 2:
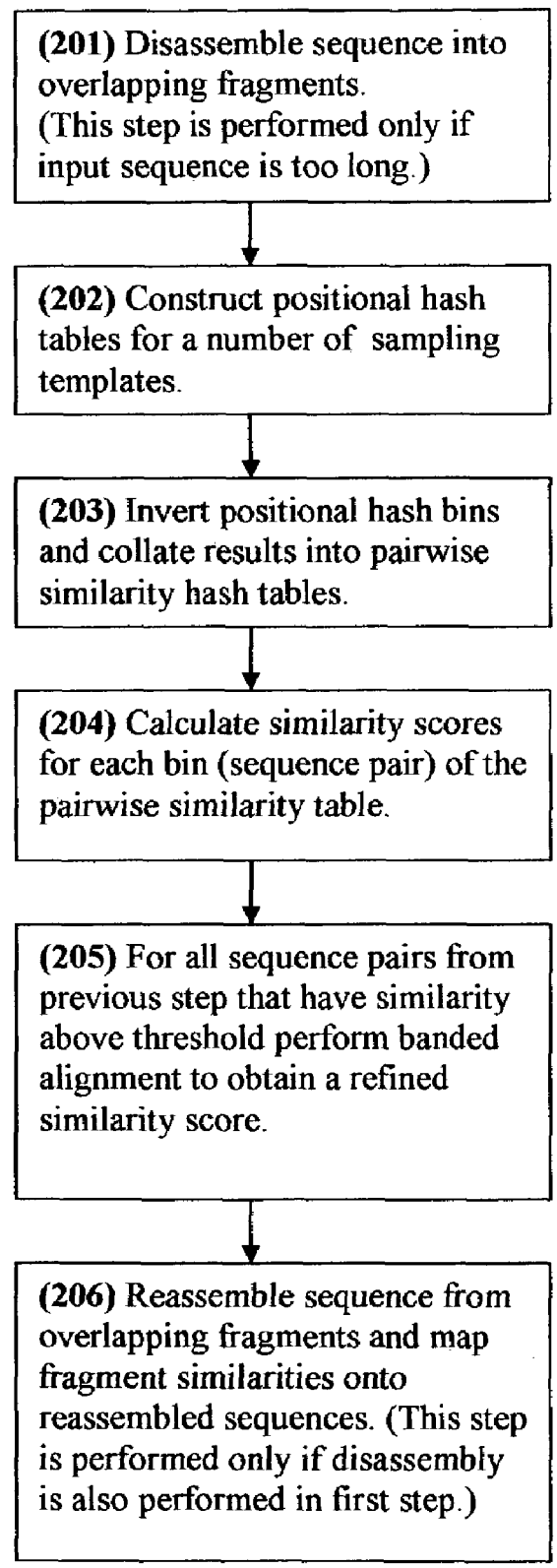
FIG. 2: Flow Chart of Positional Hashing. Steps (201) and (206) are performed only if at least one of the compared sequences is too long for direct positional hashing (the threshold of length is in the 10-10,000 bp range, typically 500 bp). Steps (202) and (203) are performed as illustrated in FIG. 1.

FIG. 2 provides a flow-chart for the full set of steps involved in a particular embodiment of Positional Hashing. Note that the first and last steps (disassembly and assembly respectively) are performed for long sequences (for example, when comparing two mammalian genomes against each other, or when comparing thousands of ESTs against a genomic sequence). Long sequences are broken into overlapping sequence fragments (sometimes referred to as "windows"), and the fragments are then be compared via Positional Hashing as already described. The fragments are reassembled back in the final step by projecting the fragmentary similarities onto the original long sequence.

An Illustrative Example of Positional Hashing

Figure 3:
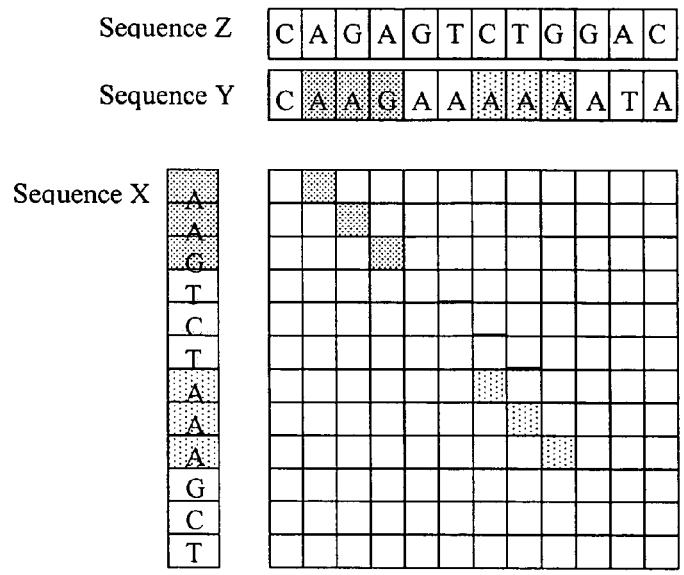
FIG. 3. The particular embodiment illustrated here assumes that Positional Hashing is used as a filter for a more refined similarity search: only the sequences that have high score in step (204) are considered for the refined search in step (205).
Figure 3:
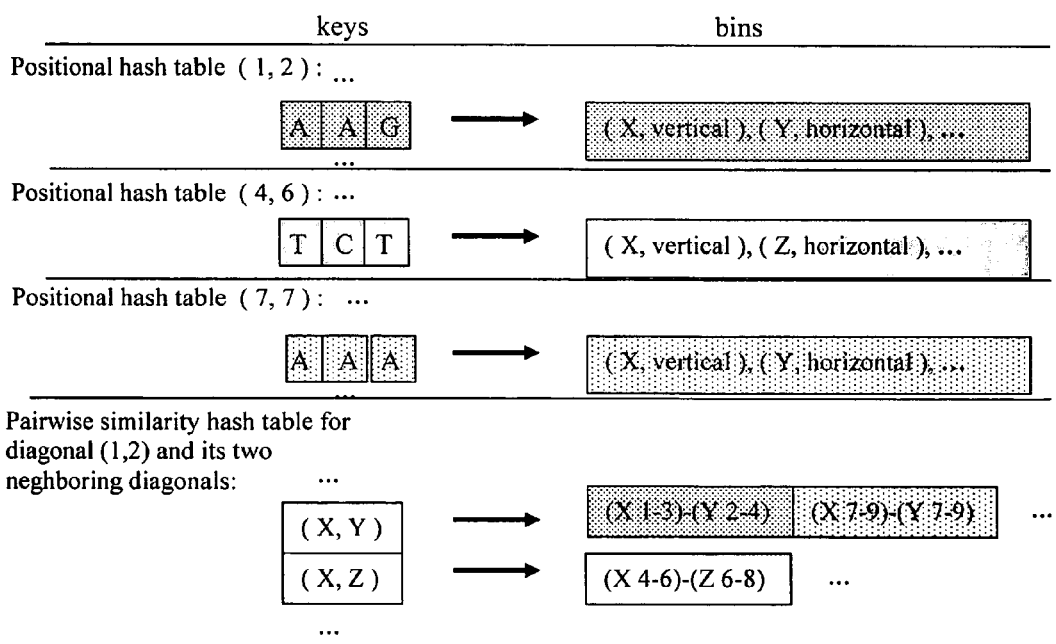

FIG. 3 illustrates an example of Positional Hashing. Three 12-basepair sequences (labeled X, Y, and Z) are compared using three sampling templates (denoted by the pairs of coordinates of their top-leftmost cells as (1,2), (4,6), and (7,7)). Note that each of the three templates consists of 3 diagonally arranged consecutive cells. The lengths of sequences and templates are selected to be deliberately small for simplicity of this illustrative example. In practice, the lengths are typically larger.

Note that the three sampling templates in FIG. 3 fall within three consecutive diagonals. In practice, a larger number of sampling templates would typically fall within each diagonal, and each diagonal would contain multiple templates. The number of templates represented in our example was selected to be small for simplicity.

The three sampling templates project horizontally and vertically into 3-letter word positions. In our example, we assume that the three-letter words in the sampled positions are used directly as keys in positional hash tables, each positional hash table corresponding to a sampling template.

While each of the three sequences is sampled both horizontally and vertically, for simplicity, FIG. 3 only illustrates vertical sampling of sequence X and horizontal sampling of sequences Y and Z. Additionally, also for simplicity, only a subset of sampled words is illustrated.

Positional hash tables corresponding to each of the three sampling templates are illustrated. Note that the following bins in the positional hash tables contain evidence of atomic similarities: "AAG" bin of positional hash table for sampling template (1,2) contains evidence of atomic similarity between sequences X and Y; "TCT" bin of (4,6) contains atomic similarity between X and X; and "AAA" bin of (7,7) contains additional atomic similarity between X and Z.

Atomic similarities are collated into pairwise similarity hash tables. The example in FIG. 3 assumes that similarity hash tables are assigned to each diagonal and that atomic similarities from sampling templates belonging to that diagonal and the two neighboring diagonals are collated together in the same similarity hash table. In particular, FIG. 3 illustrates the bin (X, Y) with the following two entries: (i) one along sampling template (1,2), indicating that the same word is present between positions 1 and 3 in X and between positions 2 and 4 in Y; and (ii) along sampling template (7,7), indicating that the same word is present between positions 7 and 9 in X and between positions 7 and 9 in Y. One entry in the bin (X, Z) is also indicated.

While FIG. 3 does not illustrate steps beyond collation, a number of specific embodiments of scoring and refinement steps exist. In one embodiment of scoring, the score is simply calculated as the number of atomic similarities (in this case the sequence pair (X, Y) would receive a score of at least 2). In one embodiment of filtering, a banded alignment is performed by dynamic programming between high-scoring pairs of sequences in order to obtain a precise alignment score and thus eliminate false positives. For example, assuming that a global banded alignment between sequences X and Y around diagonal (1,2) and including the diagonals (1,1) and (1,3) in the alignment band is performed as part of the refinement step, at least one insertion or deletion would need to be included in the alignment in order to include both the sampling templates (1,2) and (7,7) in the same alignment—this is obviously due to the fact that (1,2) and (7,7) reside on neighboring diagonals (diagonals (1,2) and (1,1) respectively).

Implementation and Benchmark Testing of Positional Hashing

Positional Hashing has been implemented in PASH program. PASH program was written using both C and Perl programming languages. For optimal speed, Positional hashing routines themselves were implemented in C. Collation step and ancillary routines were written in Perl.

The performance of the module of PASH that constructs the positional hash table was analyzed on a benchmark consisting of 16 million sequences. Since memory and time usage are based on the number of words and diagonals sampled, sampling of a single word sufficed for benchmark purposes. Our benchmark numbers are based on the hashing of one 13-mer word position on one of the diagonals on a dual-processor Intel Pentium machine with 1 GB of RAM.

Memory usage predicted based on the size of positional hashing table has been compared to actual measured memory usage. Individual steps in the hashing process have been individually timed. The time accounted for by adding the time spent in individual steps is compared to the total measured time. Finally, the results of the benchmark test have been used to estimate RAM and time required to perform comparison of multiple mammalian genomes on a cluster of 100 nodes.

Most of the RAM usage in our benchmark test falls into one of the into following three categories:

1) Read file index contains an ID (28 bits, 4 B reserved space), address (8 B), and length (2 B) of each of the (16M) sequences ("reads"), a total of 14 B per sequence. One should note that the position of the sampling template is not stored in the read file index. That information requires little extra space per each positional hash table and is not counted here.
2) Fixed hash table contains $4^{13}$ (equals approximately 67M) bins, hash table bins corresponding one-to-one to all distinct 13-mer subsequences. The fixed hash table is implemented as an array of 67M pointers. Each pointer points to a growable array of entries in the bin, as described in 3) below. A total of $4^{13}$ different growable arrays can be indexed in 26 bits and thus 4 B of memory space was reserved for each pointer.
3) The hash bin entries, a total of 16M entries, 5 B each (1 B counter+413 pointer to sequence ("read") file index). The entries from a single bin are stored in a growable array. One counter per bin suffices; thus our calculation reflects the worst-case scenario where there is at most one entry per bin. Also, the pointer to a sequence ("read") requires 28 bits, plus 1 bit to indicate whether it is sampled directly or as a reverse complement, plus 1 bit to indicate whether it is sampled in a horizontal or vertical sampling position, giving a total of 30 bits of information which is stored in 4 B of reserved space, resulting in 2 bits of extra unused space per pointer.

The total RAM usage by the hash table is obtained by adding the usage in all three categories. As the following summary indicates, the hash table usage accounts for most of the actual measured usage:

| | | | | |
|---|---|---|---|---|
| 1) | Read file index: | 16 M | * 14B | =224 MB |
| 2) | Fixed hash table: | 67 M ($4^{13}$) | * 4B | =268 MB |
| 3) | Bin entries: | 16 M | * 5B | =80 MB |
| | | | (1B counter ± 4B entry) | |
| | Total hash table: | | | =572 MB |
| | Total (measured): | | | =768 MB |

To perform the comparison between multiple mammalian genomes, each of the genomic sequences would first be broken into 500 bp reads with 250 bp overlaps, a total 6M reads per mammal, assuming typical mammalian genome size of 3 GB. This would result in a total of 12M reads for two mammals, well below the 16M used in our benchmark, thus implying that 1 GB of RAM would be more than sufficient. Moreover, by extrapolating the performance on our benchmark, we may see that even a three-way comparison (say, human, mouse and rat) is possible within 1 GB of RAM.

Most of the CPU usage in our benchmark test falls into one of the following four categories:

1) disk input/output and creation of read file index;
2) creation of fixed hash table and calculation of hash function for all the entries;
3) space allocation and storage of entries into bins; and
4) post-processing and freeing-up of hash-table space.

The accounted for processing and the actual measured time are summarized as follows:

| | | |
|---|---|---|
| 1) | Disc Input/Output: | =86 sec. |
| 2) | Creating hash table and computing hash function: | =44 sec. |
| 3) | Storing entries in hash bins: | =48 sec |
| | Total accounted for read processing time | =178 sec |
| | Total measured read processing time: | =200 sec |
| 4) | Freeing hash table space & post-processing: | =12 sec |
| | Total accounted for: | =190 sec |
| | Total measured: | =239 sec |

Using the results of the benchmark test, we predicted the performance of PASH on other large-scale sequence comparison problems. In order to complete multiple mammalian genomes, one samples on average of around 20 13-mer words in each of the 500 diagonals, a total of around 10,000 words. Assuming that the comparison is performed on a cluster consisting of 100 nodes, a total of 100 words would be hashed on each node, a total of 23,900 seconds, or about 7 hours of CPU time. Thus, under a reasonable assumption that the construction of positional hash tables takes up most of the time in a whole-genome comparison process (which also includes disassembly, inversion collation, refinement, and reassembly steps, as illustrated in FIG. 2), one concludes that a multigenome comparison of mammalian-sized genomes is performed via Positional Hashing in less than one day on a cluster consisting of 100 nodes with 1 GB RAM per node. If unassembled genomes reads are compared, due to typically higher number of reads, larger RAM would be necessary (3-4 GB).

REFERENCES

1. Collins, F., *In the crossfire: Collins on genomes, patents, and 'rivalry'*. Science, 2000. 287 (5642): p. 2396-2398.
2. Collins, F. a. M., Victor A., *Implications of the Human Genome Project for medical science*. JAMA, 2001. 285: p. 540-544.
3. Fortini, M. E. and G. M. Rubin, *Analysis of cis-acting requirements of the Rh3 and Rh4 genes reveals a bipartite organization to rhodopsin promoters in Drosophila melanogaster*. Genes & Development, 1990. 4 (3): p. 444-63.
4. O'Brien, S. J. a. E., E. and Murphy, W. J., *On choosing mammalian genomes for sequencing*. Science, 2001. 292 (5525): p. 2264-2266.
5. Green, E. D., and Chakravarti, A., *The human genome sequence expedition: views from the "base camp"*. Genome Research, 2001. 11 (5): p. 645-651.
6. VandeBerg, J. L. e. a., *Examining priorities for a primate genome project*. Science, 2000. 290 (5496): p. 1504-1505.
7. Gibbons, A., *Genomics: Building a case for sequencing the chimp*. Science, 2000. 289 (5483): p. 1267-1267.
8. Ansari-Lari, M. A., et al., *A gene-rich cluster between the CD4 and triosephosphate isomerase genes at human chromosome 12p13*. Genome Research, 1996. 6 (4): p. 314-26.

9. Ansari-Lari, M. A., et al., *Large-scale sequencing in human chromosome 12p13: experimental and computational gene structure determination*. Genome Research, 1997. 7 (3): p. 268-80.
10. Ansari-Lari, M. A., et al., *Comparative sequence analysis of a gene-rich cluster at human chromosome 12p13 and its syntenic region in mouse chromosome 6*. Genome Research, 1998. 8 (1): p. 29-40.
11. Frazer, K. A., et al., *Computational and biological analysis of 680 kb of DNA sequence from the human 5q31 cytokine gene cluster region*. Genome Research, 1997. 7 (5): p. 495-512.
12. Yung Yu, C., et al., *The human and mouse MHC class III region: a parade of 21 genes at the centromeric segment*. Immunology Today, 2000. 21 (7): p. 320-8.
13. Endrizzi, M. G., et al., *Genomic sequence analysis of the mouse Naip gene array*. Genome Research, 2000. 10 (8): p. 1095-102.
14. Dehal, P., et al., *Human chromosome 19 and related regions in mouse: conservative and lineage-specific evolution*. Science, 2001. 293 (5527): p. 104-11.
15. Rubin, G. M., et al., *Comparative genomics of the eukaryotes*. Science, 2000. 287 (5461): p. 2204-15.
16. Milosavljevic, A., *DNA Sequence Similarity Recognition by Hybridization to Short Oligomers*. 1999: U.S. Pat. No. 6,001,562.
17. Gottgens, B., et al., *Analysis of vertebrate SCL loci identifies conserved enhancers. (erratum appears in Nat Biotechnol 2000 October; 18 (10):1021)*. Nature Biotechnology, 2000. 18 (2): p. 181-6.
18. Loots, G. G., et al., *Identification of a coordinate regulator of interleukins 4, 13, and 5 by cross-species sequence comparisons. (see comments)*. Science, 2000. 288 (5463): p. 136-40.
19. Onyango, P., et al., *Sequence and comparative analysis of the mouse 1-megabase region orthologous to the human 11p15 imprinted domain. (erratum appears in Genome Res 2001 February; 11 (2):308)*. Genome Research, 2000. 10 (11): p. 1697-710.
20. Ravetch, J. V., I. R. Kirsch, and P. Leder, *Evolutionary approach to the question of immunoglobulin heavy chain switching: evidence from cloned human and mouse genes*. Proceedings of the National Academy of Sciences of the United States of America, 1980. 77 (11): p. 6734-8.
21. O'Brien, S. J., et al., *The promise of comparative genomics in mammals*. Science, 1999. 286 (5439): p. 458-62.
22. Marshall Graves, J. A., *Comparative Genomics of Vertebrates and the Evolution of Sex Chromosomes*, in *Comparative Genomics*, M. Clark, Editor. 2000, Kluwer Academic Publishers.
23. Tettelin, H., et al., *Complete genome sequence of a virulent isolate of Streptococcus pneumoniae. (see comments)*. Science, 2001. 293 (5529): p. 498-506.
24. Clark, M., ed. *Comparative Genomics*. 2000, Kluwer Academic Publishers.
25. Sankoff, D., and J. H. Nadeau, ed. *Comparative Genomics*. 2000, Kluwer Academic Publishers.
26. Potocki, L., et al., *Molecular mechanism for duplication 17p11.2—the homologous recombination reciprocal of the Smith-Magenis microdeletion*. Nature Genetics, 2000. 24 (1): p. 84-7.
27. Thomas, J. W., et al., *Comparative genome mapping in the sequence-based era: early experience with human chromosome 7*. Genome Research, 2000. 10 (5): p. 624-33.
28. Lupski, J. R., *Genomic disorders: structural features of the genome can lead to DNA rearrangements and human disease traits*. Trends in Genetics, 1998. 14 (10): p. 417-22.
29. Weber, J. L. and E. W. Myers, *Human whole-genome shotgun sequencing*. Genome Research, 1997. 7 (5): p. 401-9.
30. Adams, M. D., et al., *The genome sequence of Drosophila melanogaster*. Science, 2000. 287 (5461): p. 2185-95.
31. Altschul, S. F., et al., *Gapped BLAST and PSI-BLAST: a new generation of protein database search programs*. Nucleic Acids Research, 1997. 25 (17): p. 3389-402.
32. A. MILOSAVLJEVIC, *DNA sequence similarity recognition by hybridization to short oligomers*, 1999. U.S. Pat. No. 6,001,562.
33. J. L. WEBER AND E. W. MYERS, *Human whole-genome shotgun sequencing*, Genome Res., 7 (1997), pp. 401409.
34. P. Pevzner, *Computational Molecular Biology*, The MIT Press, Cambridge, Mass., 2000.

---

What is claimed is:

1. A method for comparing at least a first sequence and a second sequence of letters from a finite alphabet by detecting and collating at least a first similarity and a second similarity between the first sequence and the second sequence comprising the steps of:

(i) Projecting a two-dimensional sampling template onto at least a first and second sequence of fixed length, wherein the sampling template comprises a set of contiguously or non-contiguously diagonally spaced cells to thereby obtain subsequences corresponding to each of the at least first and second sequences;

(ii) calculating a discrete countable value for each of the subsequences;

(iii) creating a set of bins wherein each bin from the set corresponds to at least one of a plurality of discrete countable values;

(iv) assigning each of the separate discrete countable values to a bin in the created set of bins;

(v) if a plurality of separate discrete countable values associated with any of the at least first and second sequences are assigned to the same bin in the created set of bins, indicating a similarity between the sequences whose associated discrete countable values are in the same bin;

(vi) performing steps (i) to (v) using a template comprising a different set of contiguously or non-contiguously diagonally spaced cells than the set of the previous template;

(vii) collating any of the indicated similarities;

wherein all of steps (i) to (vii) are performed on a computer.

2. The method of claim 1, wherein said first and said second sequences are nucleic acid sequences.

3. The method of claim 1, wherein said first and said second sequences are amino acid sequences.

4. The method of claim 1, wherein said first and said second sequences are texts in English language.

5. The method of claims 2, 3 or 4, wherein said first and second sequences are contained within at least a first supersequence.

6. The method of claim 2, wherein said two sequences are at least 500 letters long and overlap by at least 250 basepairs.

7. The method of claim 1, wherein said two sequences are not contained within a common supersequence.

8. The method of claim 1, wherein similarities corresponding to at least two sampling templates along one diagonal are collated.

9. The method of claim 1, wherein similarities corresponding to at least two sampling templates along a set of at least three neighboring diagonals are collated.

10. The method of claim 1, wherein a set of bins for a first sampling template resides in random access memory of a first computer, and a set of bins for a second sampling template used for the same comparing reside in random access memory of a second computer.

11. The method of claim 10, wherein said first computer and said second computer are components of a multi-processor computer.

12. The method of claim 10, wherein said first computer and said second computer are components of a computer cluster.

* * * * *